United States Patent [19]
Wilson

[11] Patent Number: 5,380,292
[45] Date of Patent: Jan. 10, 1995

[54] GASTROINTESTINAL NEEDLE MECHANISM

[75] Inventor: Donald Wilson, Clemmons, N.C.

[73] Assignee: Wilson-Cook Medical, Inc., Winston-Salem, N.C.

[21] Appl. No.: 171,926

[22] Filed: Dec. 22, 1993

[51] Int. Cl.⁶ ............................................. A61M 25/00
[52] U.S. Cl. ...................... 604/164; 604/158
[58] Field of Search ................ 604/158, 164, 165

[56] References Cited

U.S. PATENT DOCUMENTS

| | | | |
|---|---|---|---|
| 1,527,291 | 2/1925 | Zorraquin | 604/158 |
| 4,867,745 | 9/1989 | Patel | 604/148 |
| 4,886,067 | 12/1989 | Palermo | 604/164 |
| 4,911,691 | 3/1990 | Aniuk et al. | 604/158 |
| 4,969,875 | 11/1990 | Ishikawa | 604/158 |
| 5,106,376 | 4/1992 | Moovnen et al. | 604/158 |
| 5,120,317 | 6/1992 | Luther | 604/158 |
| 5,217,441 | 6/1993 | Schichman | 604/164 |

*Primary Examiner*—Paul J. Hirsch
*Attorney, Agent, or Firm*—Woodard, Emhardt, Naughton, Moriarty & McNett

[57] ABSTRACT

An adjustable needle mechanism for gastrointestinal use in combination with an endoscope. The needle is received within a catheter or sheath and is movable between a first position in which it projects out of the catheter and a second position in which it is withdrawn into the catheter. A rotatable knob is provided to adjust the extent of projection of the needle when it is in the first position thereby eliminating any necessity to trim the end of the catheter.

5 Claims, 2 Drawing Sheets

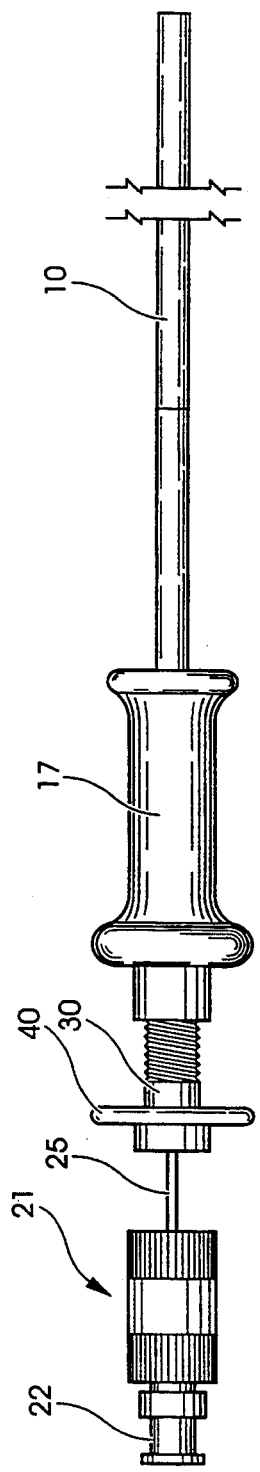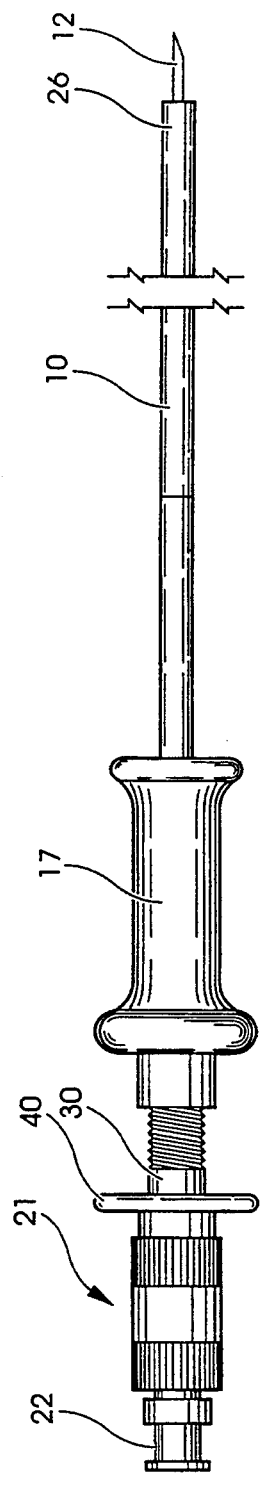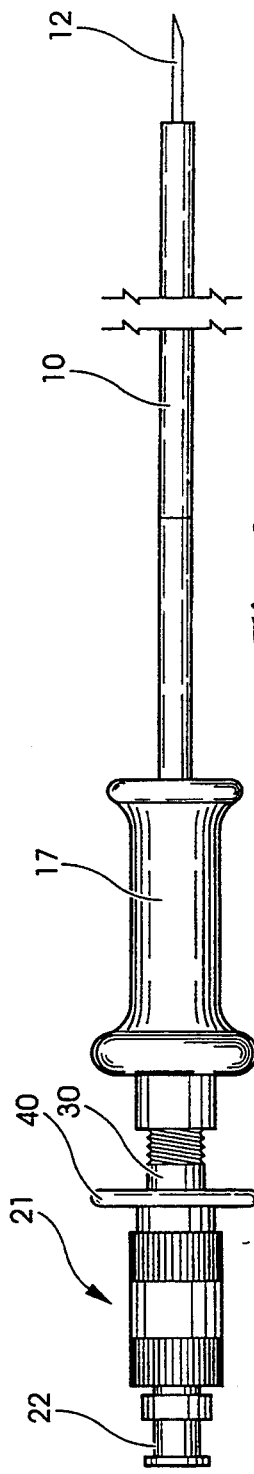

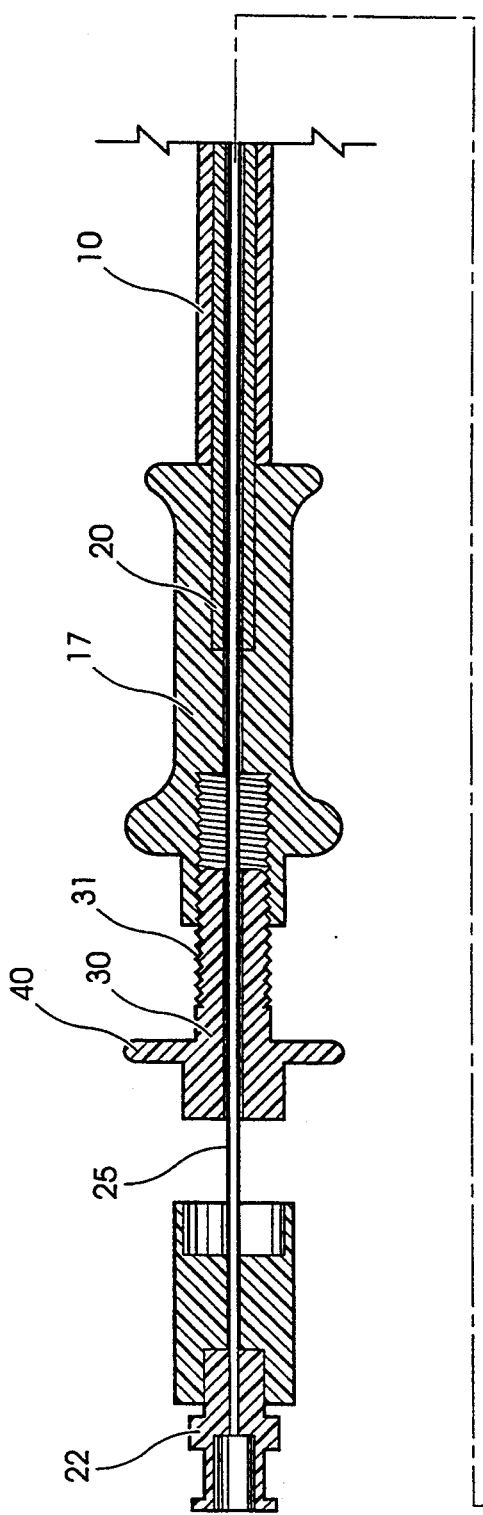
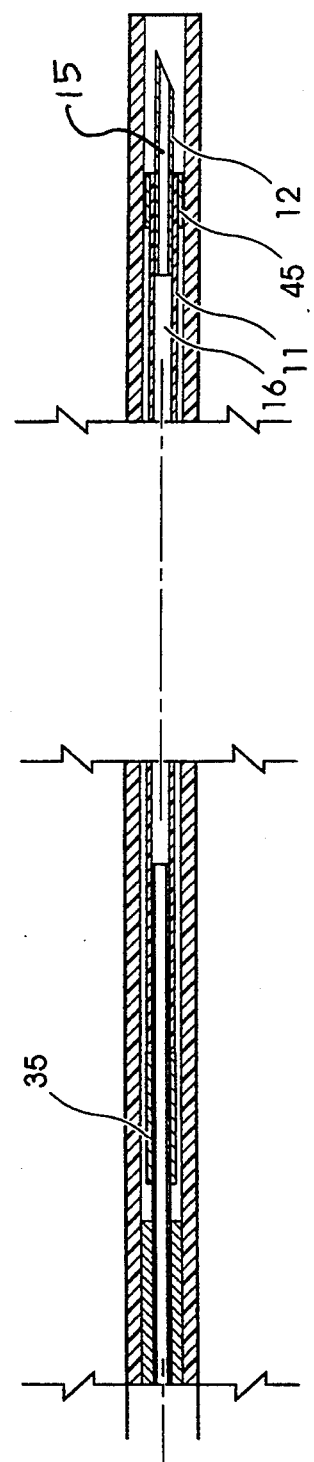
Fig. 4

GASTROINTESTINAL NEEDLE MECHANISM

BACKGROUND OF THE INVENTION

The present invention relates to an adjustable needle mechanism finding particular use in combination with an endoscope.

Endoscopes are used with injection needles to inject gastrointestinal mucosa with liquid reagents to achieve desired effects. For example, sclerosants may be injected for esophageal vatices and epinephrine may be injected to control bleeding. In order to accomplish such treatment, a needle mounted on the end of a long tube may be passed through a channel of the endoscope to inject the desired objective. The needle is shielded by a catheter within which the needle and tube are received. When the endoscope is properly located at the injection site, the needle is projected from the end of the catheter and the injection is effected.

It has been found that the length of the catheter and the tube can be affected between the time of manufacture of the mechanism and the time of use in the endoscope. For example, when the mechanism is sterilized the catheter may be lengthened or shortened or the tube may be lengthened or shortened resulting in the mechanism not projecting the needle sufficiently for proper injection of reagent. Such a problem may require the user of the mechanism to trim back the catheter before use.

Thus, the time of hospital personnel is not used effectively and damage to the mechanism may result.

It is an object of the present invention to provide an improved gastrointestinal needle mechanism. A further objective is to provide a needle mechanism which eliminates the need for trimming the catheter.

SUMMARY OF THE INVENTION

One embodiment of the present invention might involve an adjustable needle mechanism including a catheter. There is provided a tube slidable within the catheter and a head secured to one end of the catheter. A hollow needle is mounted on one end of the tube in communication with the tube. The tube is slidable in the catheter to a first position wherein the needle projects out of the other end of the catheter and is slidable in the catheter to a second position wherein the needle is withdrawn into the catheter. There is also provided a handle fixed to the tube and extending through the head. The handle has a port communicating with the tube. A handle stop member is adjustably mounted on the head in the path of the handle. The handle is movable to move the needle to the first position wherein the handle engages the handle stop member. The handle stop member is adjustable on the head to change the distance that the needle projects out of the catheter when the needle is in the first position.

BRIEF DESCRIPTION OF THE DRAWINGS

FIG. 1 is a side elevation of an adjustable needle mechanism embodying the present invention.

FIG. 2 is a view similar to FIG. 1 showing the needle projected from the catheter of the adjustable needle mechanism of FIG. 1.

FIG. 3 is a view similar to FIG. 2 showing the needle projected a greater distance from the end of the catheter.

FIG. 4 is a longitudinal sectional view of the adjustable needle mechanism.

DESCRIPTION OF THE PREFERRED EMBODIMENT

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring to the figures, a catheter or sheath 10 composed of clear plastic has slidably received therein a white plastic tube 11. The tube 11 has a hollow metal needle 12 mounted on its end so that the hollow interior 15 of the needle is in communication with the hollow interior 16 of the tube 11. A head 17 is fixed to one end of the catheter 10 by means of a metal stop member or element 20 which extends into the head 17 and also into the catheter 10 and may have suitable adhesive thereon fixing it to both the head 17 and the catheter 10.

A handle 21 includes a luer lock fitting 22 and a metal tube 25 which is fixed to the white plastic tube 11. As shown in FIG. 1 and FIG. 2 the tube 11 is movable between a first position wherein the needle projects out of the end 26 of the catheter and a second position shown in FIG. 1 wherein the needle is received within the catheter. FIG. 4 shows the tube (and needle) intermediate these two positions. The movement of the needle 12 between the positions of FIG. 1 and FIG. 2 can be accomplished by moving the handle 21 relative to the head 17. Thus when the handle 21 is pulled away from the head 17 the position of FIG. 1 is achieved while pushing of the handle 21 toward the head 17 produces the position of FIG. 2.

A stop member 30 is adjustably mounted on the head 17 in the path of the handle 21. The stop member 30 is threadedly mounted on the head 17 by means of threads 31. As shown in FIGS. 2 and 3 the position of the stop member 30 can be adjusted by screwing it into the head 17 as shown in FIG. 3 or by unscrewing it from the head 17 as shown in FIG. 2. In FIGS. 2 and 3 the handle 21 is moved against the adjustable stop 30. It can be seen in FIG. 2 that the needle 12 does not project out of the catheter 10 to the same degree that it projects out of the catheter 10 in FIG. 3. Thus the amount of projection of the needle can be controlled and set by adjusting the position of the stop member 30.

A metal collar 35 is fixed to the tube 25 and is located contiguous to the end of the white plastic tube 11. When the handle 21 is pulled as far as possible away from the head 17 to the position shown in FIG. 1 the metal collar 35 engages the metal stop 20 thus preventing further movement of the handle 21 away from the head and stop member 30.

In order to use the adjustable needle mechanism with an endoscope the needle is first withdrawn into the outer sheath or catheter 10 by fully retracting the handle 21, that is pulling it away from the head 17. A prefilled syringe is then attached to the luer lock fitting 22. The needle extension is determined by advancing the handle fully forward against the stop 30. In one embodiment of the invention it has been determined that the needle 12 should extend 5 mm from the end 26 of the catheter. If the needle does not extend the appropriate desired distance from the catheter 26, the knob 40 of the stop member 30 is rotated to cause the stop member 30 to move rightwardly as viewed in the Figs. so as to permit a greater amount of extension of the needle. If on the other hand the needle initially projects too great a distance the knob 40 can be rotated to move the stop member away from the head 17 so as to properly set the projected position of the needle.

The needle is then retracted into the sheath or catheter 26 by pulling the handle 21 to the position of FIG. 1. The adjustable needle mechanism is then introduced into the accessory channel of the endoscope using short movement increments. The needle should be kept retracted when the sheath is being advanced through the endoscope to protect the endoscope from damage. Once the mechanism is visualized in the endoscopic field of view, advancement is stopped and the target site is selected. With the sheath in endoscopic view, the needle is projected from the sheath. If the needle extension does not appear to be adequate, fine adjustment can be obtained by rotating the adjustment knob 40. The extended needle may then be inserted into the targeted tissue site and the injection completed. The needle catheter should be withdrawn from the target site into the sheath by pulling back on the handle 21 relative to the head 17 before retracting the catheter sheath through the endoscope accessory channel in order to protect the endoscope from damage.

In representative embodiments of the invention the catheter or sheath 10 had a length of 200 and 240 cm. and an O.D. of approximately 2.3 mm otherwise known as 7 French. The inner tube 11 has a 4 French size or, in other words, an approximate 1.35 mm O.D. The needle 12 is either a 23 or 25 gauge needle and has a crimped section 45 of cannula securing it to the end of the tube 11. The cannula 45 is shown with a slightly larger O.D. than actual in order to make it visible in FIG. 4. It should be understood, however, that the O.D. is sufficiently small to allow it to slide easily in the catheter 10.

It can be appreciated that the mechanism of this invention provides an improved needle mechanism which eliminates the necessity of trimming the end of the catheter. It will also be evident that the present device provides the additional advantage of allowing adjustment of the amount of projection of the needle from the sheath when the mechanism is in use and is projecting from the endoscope.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An adjustable needle mechanism comprising
   a catheter;
   a first tube slidable within said catheter;
   a head secured to one end of said catheter
   a hollow needle mounted on one end of said tube in communication with said tube, said tube being slidable in said catheter to a first position wherein said needle projects out of the other end of said catheter and slidable in said catheter to a second position wherein said needle is withdrawn into said catheter;
   a handle fixed to said tube and extending through said head, said handle having a port communicating with said tube;
   a handle stop member adjustably mounted on said head in the path of said handle;
   said handle being movable to move said needle to said first position wherein said handle engages said handle stop member, said handle stop member being adjustable on said head to change the distance that said needle projects out of said catheter when said needle is in said first position.

2. The adjustable needle mechanism of claim 1 wherein said stop member is threadedly mounted on said head, said stop member being adjustable to change the distance of said needle projection by screwing said stop member into or out of said head.

3. The adjustable needle mechanism of claim 2 wherein said handle includes a metal tube extending from said port through said stop member and head into said first tube, said metal tube being fixed within said first tube.

4. The adjustable needle mechanism of claim 3 additionally comprising:
   a tubular metal stop element slidably receiving said metal tube and fixed to said head, and
   a metal collar fixedly received on said metal tube and arranged to engage said tubular metal stop element when said first tube is in said second position.

5. The adjustable needle mechanism of claim 4 wherein said handle includes a luer lock fitting which provides said port, said luer lock fitting being fixed to said metal tube.

* * * * *